US012298264B2

(12) United States Patent
Masters et al.

(10) Patent No.: US 12,298,264 B2
(45) Date of Patent: May 13, 2025

(54) MEASURING DEFLECTION TO DETERMINE A CHARACTERISTIC OF A LAYERED-MATERIAL STRIP

(71) Applicant: United States of America as Represented by The Secretary of the Army, Alexandria, VA (US)

(72) Inventors: Benjamin C Masters, Urbana, IL (US); Rebekah C Wilson, Mahomet, IL (US)

(73) Assignee: UNITED STATES OF AMERICA AS REPRESENTED BY THE SECRETARY OF THE ARMY, Alexandria, VA (US)

( * ) Notice: Subject to any disclaimer, the term of this patent is extended or adjusted under 35 U.S.C. 154(b) by 177 days.

(21) Appl. No.: 16/588,710

(22) Filed: Sep. 30, 2019

(65) Prior Publication Data

US 2021/0131985 A1     May 6, 2021

(51) Int. Cl.
| | |
|---|---|
| *G01N 25/16* | (2006.01) |
| *G01N 21/17* | (2006.01) |
| *G01N 33/20* | (2019.01) |
| G01N 21/84 | (2006.01) |

(52) U.S. Cl.
CPC ............. *G01N 25/16* (2013.01); *G01N 21/17* (2013.01); *G01N 33/20* (2013.01); *G01N 2021/1725* (2013.01); *G01N 2021/1731* (2013.01); *G01N 2021/8438* (2013.01)

(58) Field of Classification Search
CPC ........ G01N 25/16; G01N 21/17; G01N 33/20; G01N 2021/1725; G01N 2021/1731; G01N 2021/8438; G01N 33/208; G01N 25/34; G01N 2203/0051; G01N 25/482;
(Continued)

(56) References Cited

U.S. PATENT DOCUMENTS

| | | | | |
|---|---|---|---|---|
| 4,526,471 A | * | 7/1985 | Bykov | ................. G01B 11/002 356/616 |
| 4,889,425 A | * | 12/1989 | Edwards | ................. G01B 11/16 356/400 |

(Continued)

FOREIGN PATENT DOCUMENTS

| | | | | | |
|---|---|---|---|---|---|
| JP | H0610917 U | * | 2/1997 | ............. | G02B 26/10 |
| JP | H10206437 A | * | 8/1998 | ............. | G01N 37/00 |
| WO | WO-2016138935 A1 | * | 9/2016 | ......... | G01B 11/0633 |

*Primary Examiner* — Mohamed K Amara
(74) *Attorney, Agent, or Firm* — Brian C. Jones

(57) ABSTRACT

Disclosed are methods that, by not physically touching a material being measured, can measure the material's differential response quite accurately. A collimated light shines on the material under test is reflected off it, and is then captured by a device that records the position where the reflected light is captured. This process is done both before and after the material is processed in some way (e.g., by applying a coat of paint). The change in position where the reflected light is captured is used in calculating the deflection of the material as induced by the process. This measured induced deflection is then used to accurately determinate the stress introduced into the material by the process. Other characteristics of the material under test, such as aspects of the material composition of a bi-metallic strip, for example, may also be determined from a deflection measurement.

20 Claims, 14 Drawing Sheets

(58) Field of Classification Search
CPC ....... G01B 11/16; G01L 5/0047; B82Y 35/00; G01Q 60/38
See application file for complete search history.

(56) References Cited

U.S. PATENT DOCUMENTS

| | | | | |
|---|---|---|---|---|
| 5,002,396 A * | 3/1991 | Ozawa | ................... | G01S 17/06 |
| | | | | 356/622 |
| 5,118,955 A * | 6/1992 | Cheng | ............... | H01L 21/67288 |
| | | | | 356/613 |
| 5,224,376 A * | 7/1993 | Elings | ................... | B82Y 35/00 |
| | | | | 977/851 |
| 5,227,641 A * | 7/1993 | Cheng | ................. | G01B 11/306 |
| | | | | 356/613 |
| 5,450,746 A * | 9/1995 | Howard | ................. | B82Y 35/00 |
| | | | | 850/52 |
| 5,546,811 A * | 8/1996 | Rogers | ................. | G01L 5/0047 |
| | | | | 73/762 |
| 5,675,154 A * | 10/1997 | Lindsay | ................. | G01Q 20/02 |
| | | | | 850/17 |
| 5,737,086 A * | 4/1998 | Gerber | ................. | G01N 25/482 |
| | | | | 356/432 |
| 6,134,971 A * | 10/2000 | Misra | ....................... | G01B 7/16 |
| | | | | 73/777 |
| 6,293,027 B1 * | 9/2001 | Elliott | ................... | G01B 11/002 |
| | | | | 33/286 |
| 6,642,517 B1 * | 11/2003 | Ghislain | ................ | G01Q 20/02 |
| | | | | 250/306 |
| 6,935,165 B2 * | 8/2005 | Bashir | ..................... | C12Q 1/00 |
| | | | | 73/64.53 |
| 8,706,428 B1 * | 4/2014 | Righi | .................... | G01B 11/16 |
| | | | | 702/34 |
| 9,163,216 B1 * | 10/2015 | Hickman | ............. | C12N 5/0658 |
| 10,386,360 B2 * | 8/2019 | Hickman | ........... | G01N 33/5061 |
| 11,209,369 B2 * | 12/2021 | Wilson | ............... | G01N 21/8422 |
| 2003/0065452 A1 * | 4/2003 | Hickman | ............... | C12Q 1/001 |
| | | | | 702/19 |
| 2004/0076961 A1 * | 4/2004 | Lewis | .................. | C12Q 1/6837 |
| | | | | 435/6.12 |
| 2005/0255448 A1 * | 11/2005 | Majumdar | ........... | G01N 29/036 |
| | | | | 435/287.1 |
| 2006/0058607 A1 * | 3/2006 | Garcia-Webb | .......... | G01N 3/38 |
| | | | | 600/407 |
| 2007/0220978 A1 * | 9/2007 | Su | ...................... | G01N 29/0681 |
| | | | | 73/632 |
| 2012/0161431 A1 * | 6/2012 | Vulpius | ................. | B29C 55/065 |
| | | | | 156/196 |
| 2014/0092717 A1 * | 4/2014 | Tokutomi | ............... | G01Q 60/08 |
| | | | | 369/53.38 |
| 2014/0223612 A1 * | 8/2014 | Proksch | ................. | G01Q 10/04 |
| | | | | 850/1 |
| 2016/0003806 A1 * | 1/2016 | Parker | ................ | G01N 33/5061 |
| | | | | 506/10 |
| 2017/0241254 A1 * | 8/2017 | Jung | ........................ | G01N 3/20 |
| 2018/0095073 A1 * | 4/2018 | Hickman | ........... | G01N 33/4833 |
| 2019/0225485 A1 * | 7/2019 | Ziegler | .................. | G01Q 60/38 |
| 2020/0320159 A1 * | 10/2020 | Matthews | ................ | C09K 5/10 |
| 2021/0003554 A1 * | 1/2021 | Hickman | ............. | G01N 33/502 |
| 2021/0096084 A1 * | 4/2021 | Wilson | .................. | G01L 5/0047 |
| 2021/0164928 A1 * | 6/2021 | Lubinski | ............ | G01N 29/2418 |
| 2021/0215675 A1 * | 7/2021 | Sun | ........................ | G01N 21/64 |
| 2022/0018786 A1 * | 1/2022 | Wilson | .................. | G01L 5/0047 |

* cited by examiner

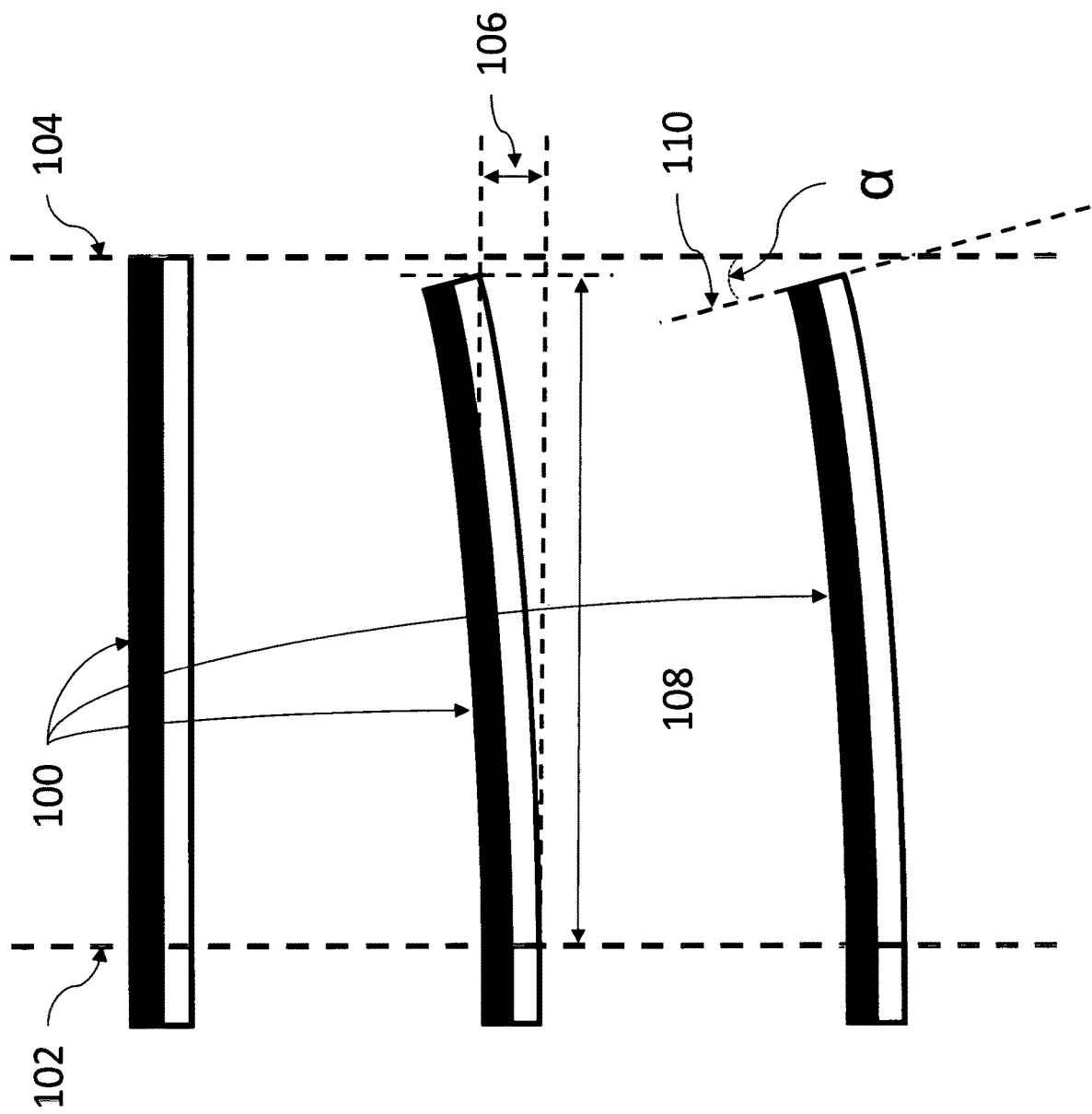

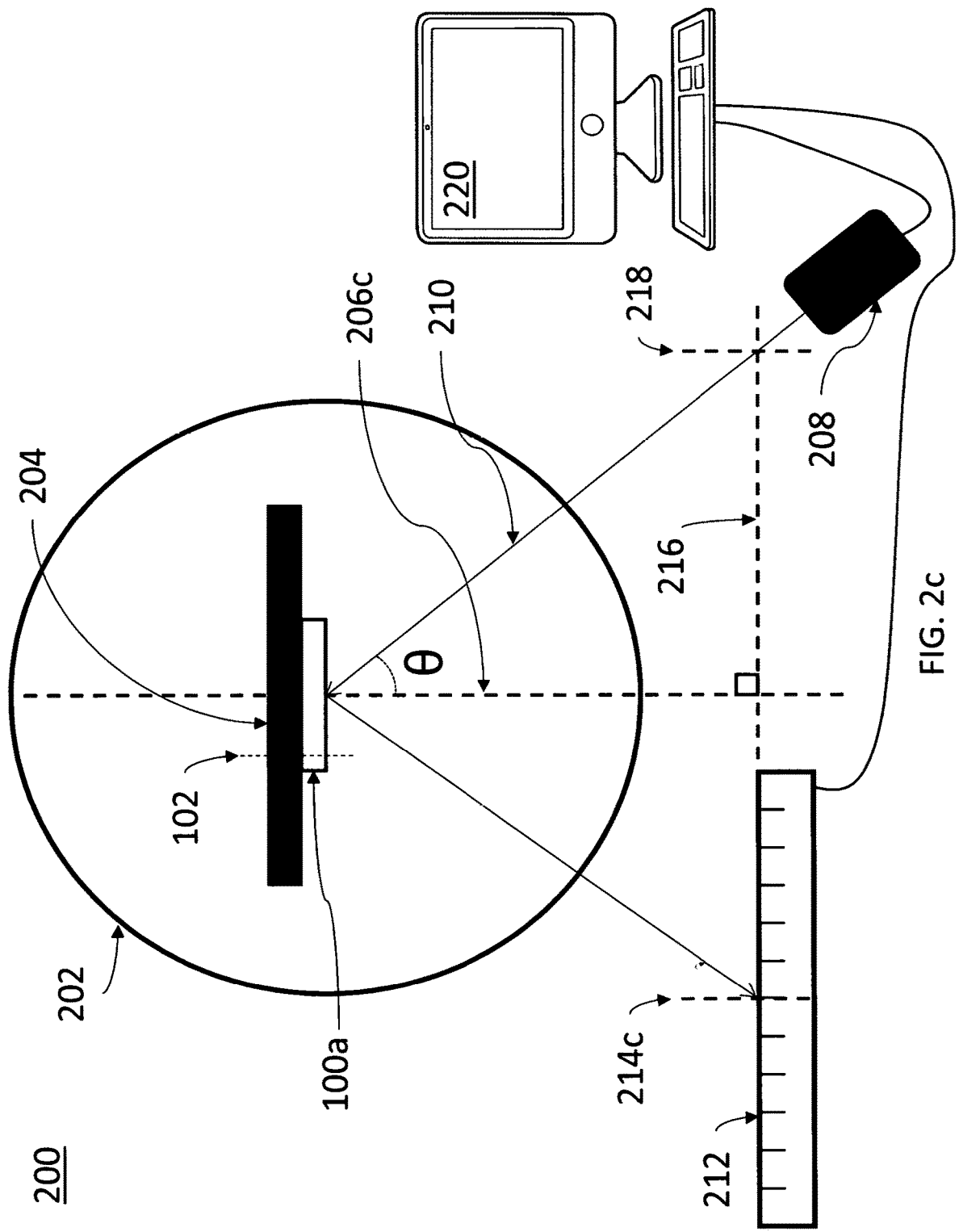

MEASURING DEFLECTION TO DETERMINE A CHARACTERISTIC OF A LAYERED-MATERIAL STRIP

FEDERALLY SPONSORED RESEARCH OR DEVELOPMENT

Under paragraph 1(a) of Executive Order 10096, the conditions under which this invention was made entitle the Government of the United States, as represented by the Secretary of the Army, to an undivided interest therein on any patent granted thereon by the United States. This and related patents are available for licensing to qualified licensees.

CROSS-REFERENCE TO RELATED APPLICATIONS

The present application is related to U.S. patent applications Ser. Nos. 16/588,185 & 16/588,943, filed of even date herewith, which are incorporated herein in their entirety by reference.

BACKGROUND

Field of the Invention

The present disclosure is related generally to metrology and, more particularly, to precision measurement of physical properties.

Description of the Related Art

This section introduces aspects that may help facilitate a better understanding of the invention. Accordingly, the statements of this section are to be read in this light and are not to be understood as admissions about what is prior art or what is not prior art.

Many machine parts are crafted from a single material, such as a machine screw made of steel. However, in some circumstances, the properties desired for the part are achieved by combining, often by layering, multiple materials of differing physical characteristics into the resultant part. As a much simplified example, car body panels are often made of steel which has many useful properties, including strength and ductility, but steel is susceptible to rust. To make a useful body panel, the steel is covered with a layer of primer and a layer of paint that together shield the steel from environmental oxygen and thus prevent rust. None of the layers by itself provides all of the panel's desired characteristics, but each adds its own beneficial characteristics to the complete body panel.

Layering materials introduces new concerns, however. In many cases, the different materials in adjacent layers react differently to environment factors such as temperature. As, for example, different materials in the layers expand and contract differently over time, the result can be paint flaking off an external structure, such as a steel highway bridge. In some cases, the manufacturing process of combining layers of different materials produces stress in the completed part. Consider a bare aluminum sheet to which is added a layer of liquid paint. The paint tends to shrink (or in some cases to expand) as it cures and, because the paint layer adheres to the aluminum layer, the curing process introduces stress into the aluminum that may warp and weaken the finished product.

The differential responses of the layers are sometimes used to good effect as when two layers of different metals are combined to make a bi-metallic strip. Due to the different properties of the two metals, the bi-metallic strip curves in a well defined manner when the temperature changes. This property of the strips has long been used in mechanical thermometers and thermostats.

BRIEF SUMMARY

The differential responses of the layers in a multi-layered material can be very important even when these responses are quite small. Difficulties arise when trying to measure these small responses, because the response to be measured can be overwhelmed by extraneous forces introduced in the measuring process, extraneous forces such as gravity and stresses introduced by the measuring process itself. Methods are here described that, by not physically touching the material being measured, can measure the differential response quite accurately.

A collimated light shines on the material under test, is reflected off it, and is then captured by a device that records the position where the reflected light is captured. This process is done both before and after the material is processed in some way (e.g., by applying a coat of paint). The change in position where the reflected light is captured is used in calculating the deflection of the material as induced by the process. This measured induced deflection is then used to accurately determinate the stress introduced into the material by the process.

In some embodiments, the deflection is measured repeatedly over time as the process matures (e.g., as the paint dries) to plot how the induced stress changes.

In some embodiments, other characteristics of the material under test ("other" here including "other than induced stress") may be determined from a deflection measurement. Aspects of the material composition of a bi-metallic strip, for example, can be determined from deflection under carefully controlled conditions without physically touching the cantilever during the measurement process.

BRIEF DESCRIPTION OF THE SEVERAL VIEWS OF THE DRAWINGS

While the appended claims set forth the features of the present techniques with particularity, these techniques, together with their objects and advantages, may be best understood from the following detailed description taken in conjunction with the accompanying drawings of which:

FIGS. 1a, 1b, 1c, and 1d are simple side- and end-views of a layered-material strip;

FIGS. 2c through 2e are schematics of the same system as in FIGS. 2a and 2b but using a "side-clamp" mount;

DETAILED DESCRIPTION

Figure 1D:
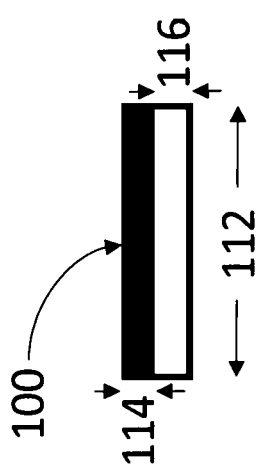

Detailed illustrative embodiments of the present invention are disclosed herein. However, specific structural and functional details disclosed herein are merely representative for purposes of describing example embodiments of the present invention. The present invention may be embodied in many alternate forms and should not be construed as limited to only the embodiments set forth herein. Further, the terminology used herein is for the purpose of describing particular embodiments only and is not intended to be limiting of example embodiments of the invention.

As used herein, the singular forms "a," "an," and "the" are intended to include the plural forms as well, unless the context clearly indicates otherwise. It further will be understood that the terms "comprises," "comprising," "includes," and "including" specify the presence of stated features, steps, or components but do not preclude the presence or addition of one or more other features, steps, or components. It also should be noted that in some alternative implementations, the functions and acts noted may occur out of the order noted in the figures. For example, two figures shown in succession may in fact be executed substantially concurrently or may sometimes be executed in the reverse order, depending upon the functionality and acts involved.

The strip 100 is depicted in FIG. 1a as having two layers, one shown in black, the other in white, and the two layers may be of different compositions. For example, the "layered-material" strip 100 may be a bi-metallic strip with one layer of steel and the other layer of brass. In another example, one layer is aluminum and the other layer is a coating of paint applied to the aluminum.

Other phrases used for the strip 100 include "cantilever," "coupon," "target," and "material under test."

While layered-material strips are discussed throughout this application, and are often discussed as having exactly two layers, some aspects of the present invention apply to strips composed of a single material or that have more than two layers.

The strip 100 is cantilevered, that is to say, it is supported at only one end. When the strip 100 is clamped in place at point 102, the portion of the strip 100 depicted in FIG. 1a to the left of 102 cannot move, but the portion to the right of that point 102, called the free end 104, is free to move.

While the strip 100 is flat in FIG. 1a, the free end 104 noticeably curves up in FIG. 1b. There are many possible forces that could lead to such curving. A bi-metallic strip 100 may curve in a well defined manner as the temperature changes due to the different characteristics of the two layers in the strip 100. In another example, a newly applied paint layer (here, the black upper layer) may shrink as it cures, and that shrinkage may pull the underlying substrate (here the lower white layer) into a curve.

The curvature can even be dynamic, as when the cantilevered strip 100 is set to vibrating. In that case, generally speaking, the strip 100 curves up and then down symmetrically around the flat position shown in FIG. 1a, the vibration occurring at a frequency characteristic of the strip 100.

There are two interdependent aspects of the curvature of the strip 100. In FIG. 1b, the curvature's deflection amount 106 is measured at a distance 108 from the clamping point 102. While for clarity's sake the deflection 106 is shown as measured at the free end 104 of the strip 100 in FIG. 1b, there is nothing special about this choice: The curvature can be characterized knowing the deflection 106 at any distance 108 from the clamping point 102.

While the deflection 106 is shown as measured from the "bottom" of the strip 100 in FIG. 1b, it could just as easily be measured from the top, the two measurements being interchangeable as long as the strip 100 does not change in thickness as it curves.

FIG. 1c illustrates another aspect of the curvature of the strip 100. In the flat strip of FIG. 1a, the normal to the surface of the strip 100 is the line 104. However, when the strip 100 curves, the curvature changes the position of the surface of the strip 100, and that changes the normal taken at the endpoint of the strip 100 from the line 104 to the line 110. The "tilt" angle between the flat-strip normal 104 and the curved-strip normal 110 is denoted as α. Small-angle approximations show that:

$$\tan(\alpha) \approx 2 * \text{deflection } 106/\text{distance } 108 \qquad \text{Equation 1}$$

Note that the normal line 110 and thus the angle a are different for each point along the curved strip 100. Note also that the curvature and thus the angle a are enlarged for clarity's sake. In a real world situation, it would be unlikely that they would be as large as shown in FIG. 1c.

FIG. 1d is an end-view of the strip 100. The strip 100 is shown with a constant width 112; the top layer has a constant thickness 114; and the bottom layer has a constant thickness 116. The two thicknesses 114, 116 can be very different from one another. Most often in this discussion, the strip 100 has a constant width 112 throughout its length, and the layers have constant thicknesses 114, 116. Some aspects of the present disclosure apply to strips 100 whose width 112 or layer thicknesses 114, 116 are not constant.

Figure 2A:
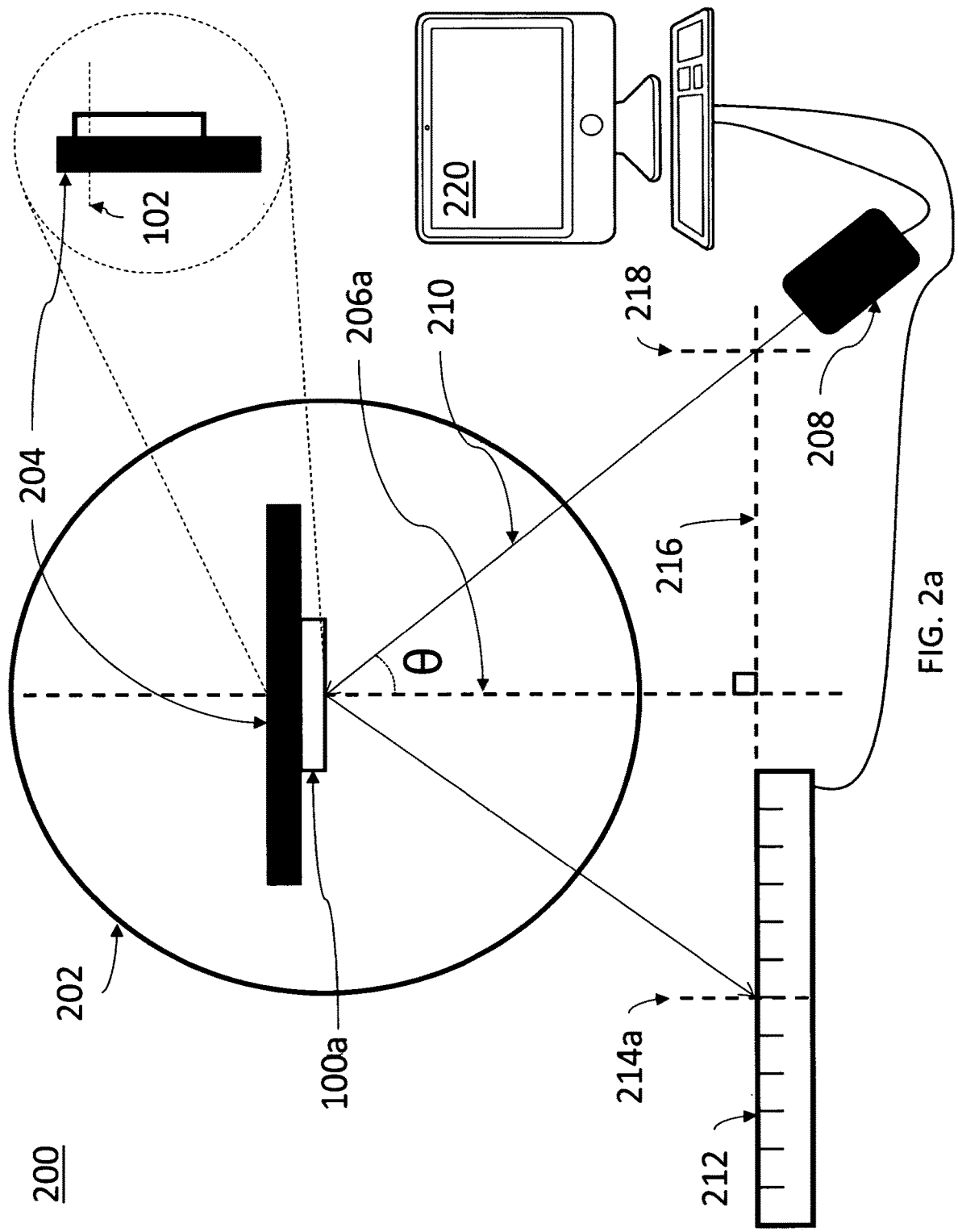
FIGS. 2a and 2b are schematics of a system for measuring deflection, the system using a "top-clamp" mount.
Figure 2B:
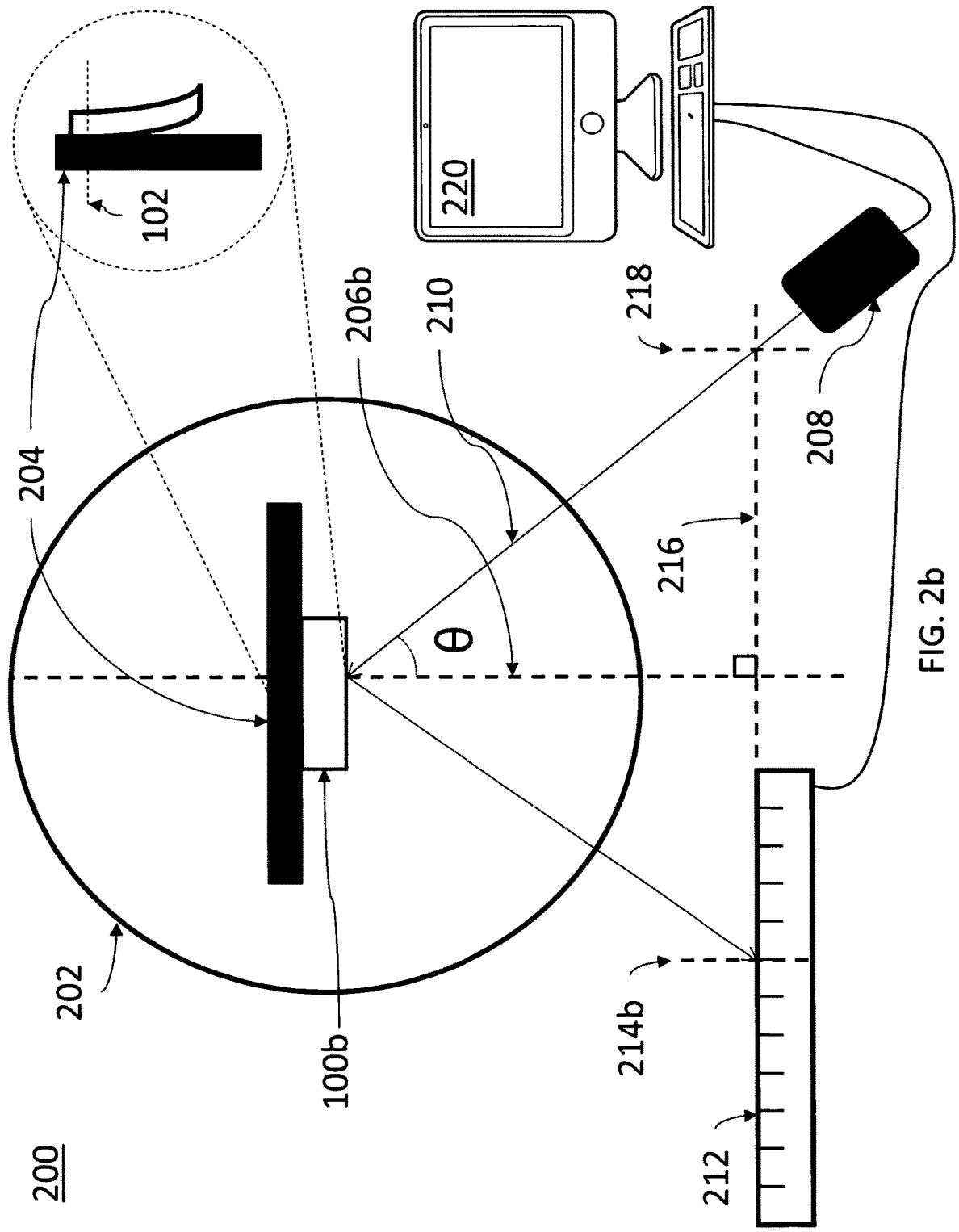
Figure 2D:
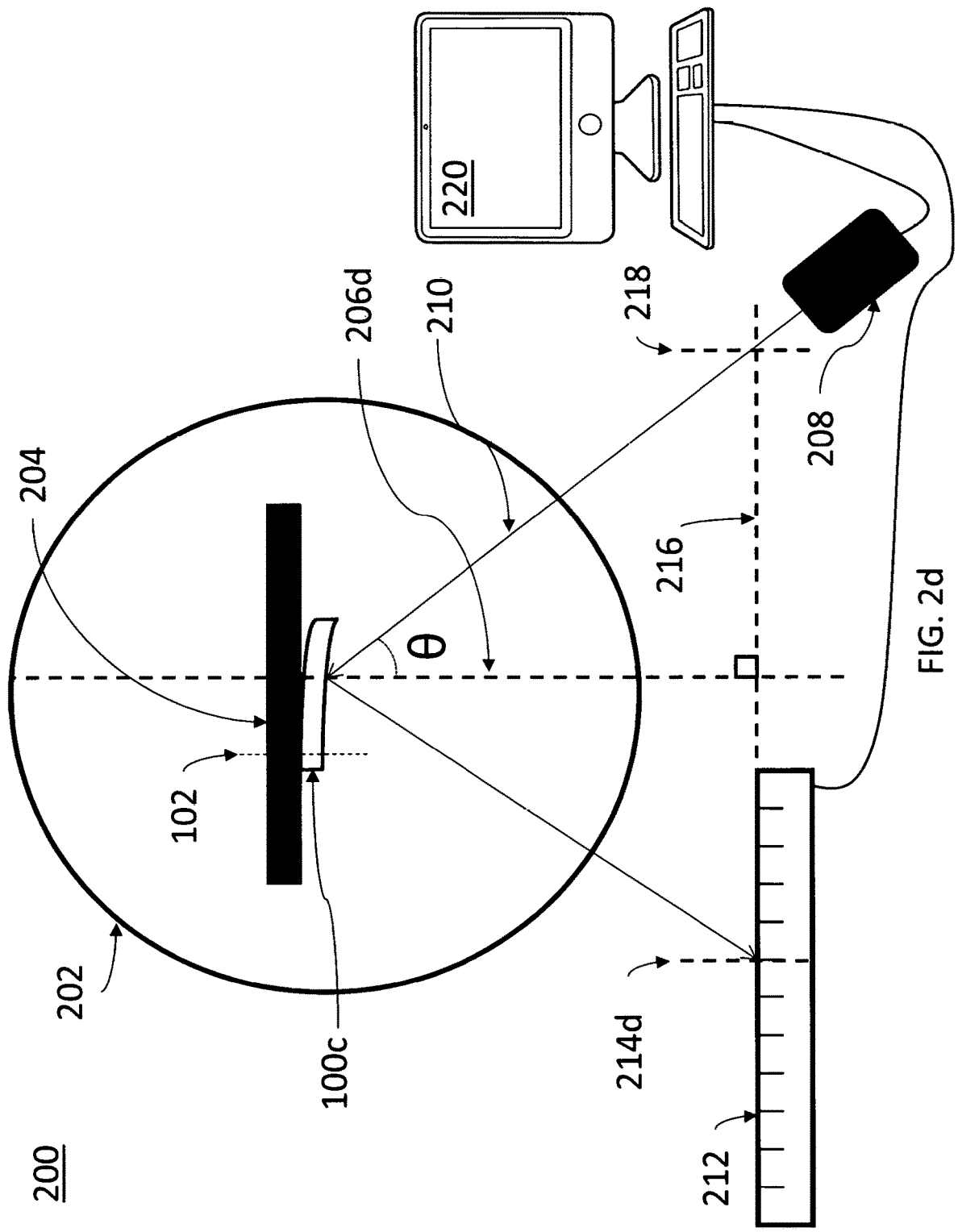
Figure 2E:
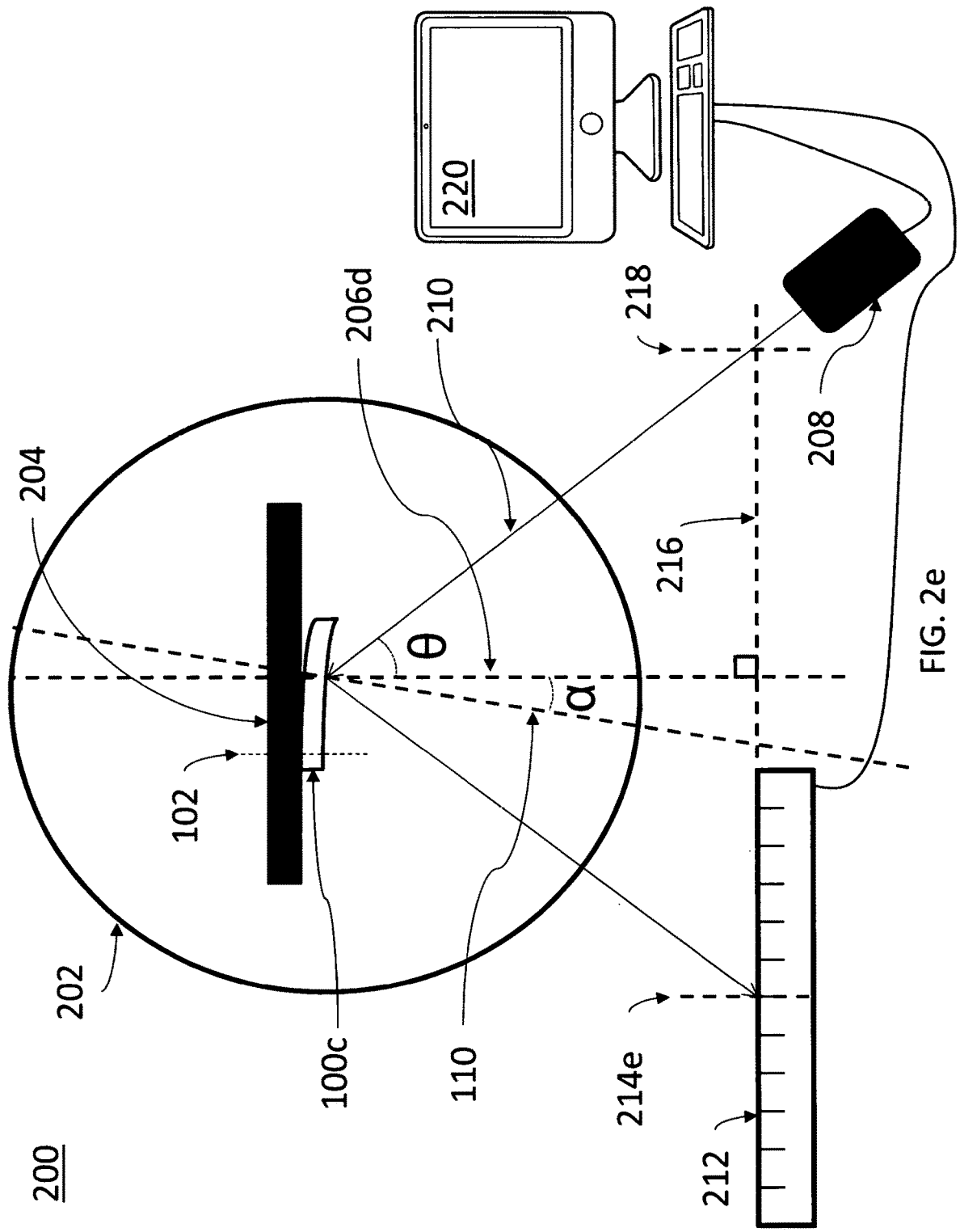

A representative system 200 for determining a characteristic of the strip 100 is shown in FIGS. 2a through 2e. The view of the representative system 200 in FIGS. 2a and 2e is from above, that is to say, gravity pulls downward into the page.

For purposes of clarity in this discussion, some reference numericals in FIGS. 2a through 2e include a suffix "a," "b," etc., when they refer to one specific figure but lack the suffix when they refer to all of the figures in general. For example, the strip is numbered "100a" in FIG. 2a and "100b" in FIG. 2b but simply "100" in the present discussion when no distinction is being drawn among the figures.

The components of the system 200 are organized around a platform 202. In some embodiments, the platform 202 is an optical table or a rotating platform supported by an optical table. On the platform 202 is a mount 204 that holds the strip 100. To make the geometry easier, some embodiments allow the incident surface of the strip 100 to be placed in the center of the platform 202. In some situations, it is important that the strip 100 be removable from the mount 204 and later replaceable on the mount 204. with the location of the strip 100 on the mount 204 substantially reproducible. In some embodiments, this property is satisfied by using a kinematic or gimbal mount 204.

In the embodiment of FIGS. 2a and 2b, the strip 100 is clamped on its top. This is illustrated by the inset drawing on the top right of these figures. In the inset, top is toward the top of the page (unlike in the overall drawing). The clamping point is shown at 102, and the portion of the strip 100 below the clamping point 102 is free to move.

The "normal" to the surface of the strip 100a taken at the point of light incidence (see discussion of 210 below) is denoted by the dotted line 206a. As discussed below, in some situations this line is not exactly normal but is within a very small angle to the normal.

A source of collimated light (e.g., a laser) 208 directs light 210 to the strip 100a. The directed light 210 hits the strip 100a at an angle θ to the normal 206a. In some embodiments, the angle θ is adjustable by increasing or decreasing the distance of 208 and 212 from 100b, for example in embodiments of the invention by rotating the platform 202. In any case, the angle θ is a known quantity, possibly read off a gauge attached to the platform 202.

The directed light 210 reflects off the strip 100a according to the well known property: "The angle of reflection [θ] is equal to the angle of incidence [θ]." Sometimes, it is useful to increase the reflectivity of the strip 100 by putting a piece of thin, highly reflective material (not shown) or by polishing part of the surface at the point of incidence. The reflected light 210 is then received at a position-sensitive light detector 212 which reports the position 214a where the reflected light 210 is received.

To explain the geometry as simply as possible, a horizontal dotted "baseline" 216 is drawn in FIG. 2a perpendicular to the normal line 206a. In FIG. 2, the baseline 216 is drawn coincident with the light-detection surface of the position-sensitive light detector 212, and the light source 208 is shown "below" the baseline 216. These choices are made purely for illustrative purposes and in no way constrain the actual implementation of the system 200.

Generally speaking, FIG. 2a illustrates the set-up for the strip 100a before it is processed in some way. In this simple case, because the strip 100a is flat, the position of the received light 214a is exactly the same distance (to the left in FIG. 2a) from the normal line 206a as the distance from the normal line 206a to the place (on the right) where the collimated light 210 originally crosses the baseline 216 line at position 218.

Many embodiments of the system 200 include a computer 220 that controls the operation of the system 200 or that at the very least receives results. The lines between the computer 220 and the light source 208 and between the computer 220 and the position-sensitive light detector 212 indicate these control and data-capture functions.

In various embodiments, the computer 220 is also configured for performing computations associated with determining characteristics of the strip 100. For example, the computer 220 may use the inputs of the angle θ and outputs 214 of the position-sensitive light detector 212 to calculate a deflection 106 in the strip 100b (see FIGS. 1b and 2b). It may then use that deflection 106 as an input into calculating a stress induced into the strip 100b. With multiple outputs 214 from the position-sensitive light detector 212, the computer 220 may create a plot of deflection 106 vs. time. These and other services performed by the computer 220 are discussed in greater detail below.

To avoid clutter some optional aspects of the system 200 are not shown. The system 200 can be made more complicated by adding environmental sensors such as a clock, thermometer, hygrometer, etc. The outputs of these sensors could be directed to the computer 220. For example, the computer 220 could record when a specific measurement is made either by timing the operation of the light source 208 or by timing the reception of position data 214 from the position-sensitive light detector 212. The system 200 could also include environmental control systems such as a heater/air conditioner to set the temperature of the strip 100 during measurement.

Because for many embodiments an accurate determination of the position of light reception 214 is a key to accurately determining a characteristic of the strip 100, the entire system 200 can be placed in a light box to shield it from extraneous light. Similarly, the measurements made by the system 200 are often very small, so the entire system 200 can be vibration-isolated from the rest of the world.

FIG. 2b depicts the situation of the strip 100b after some processing. Comparing FIG. 2b to FIG. 2a, the fundamental change is in the physical configuration of the strip 100b. Rather than being flat, the strip 100b has deflected a small amount 106 (see FIG. 1b and the inset to FIG. 2b). As discussed above, different circumstances lead to different causes for such a deflection 106. If the strip 100b is a layered-material strip, then differential responses of its layers to, for example, a temperature change, may cause the strip 100b to curve and deflect. In another example, a vibrating strip 100b would deflect in one direction, pass through a midpoint as shown by the strip 100a in FIG. 2a, then deflect in the other direction (not shown), cycling through these positions at the strip's characteristic vibration frequency.

In any case, if the strip 100b is deflected toward the baseline 216 as shown in the inset to FIG. 2b, then the directed collimated light 210 hits the strip 100b a little "lower" (with respect to the orientation of FIG. 2b) than it does in the configuration of FIG. 2a. (Note that the deflection 106 depicted in FIG. 2b is greatly exaggerated for illustration's sake: Actual deflections are expected to be much smaller.)

While the incident angle θ is unchanged from FIG. 2a to FIG. 2b, the deflection of the strip 100b toward the baseline 216 moves the normal line at the point of light incidence 206b to the right (as compared with the normal line 206a of FIG. 2a) and changes the light-reception position to 214b (also moved slightly to the right of FIG. 2a's 214a).

(Note that the deflection 106 of the strip 100b also moves the light-reception position slightly "upward and out of the page" of FIG. 2b. This tiny effect is generally not important as it does not affect the light-reception position 214b. If it were to become important, then the mount 204 would allow the strip 100b to be tilted slightly "downward and into the page" of FIG. 2b to cancel the effect before taking the measurement 214b.)

Further details of these geometric changes and their significance are discussed below in relation to step 318 of FIG. 3b.

The system 200 of FIG. 2c is the same as that of FIG. 2a, but here a side clamp is used instead of a top clamp The portion of the strip 100a to the right of the clamping point 102 is free to move. Because the strip 100a is flat in FIG. 2c, the geometry is the same as that of FIG. 2a, that is, incident angle θ, normal 206c, and light-reception position 214c are all the same as their counterparts in FIG. 2a.

In FIGS. 2e and 2e, the pre-processed strip 100a has become the processed strip 100c with a deflection 106. Because of the side-clamping arrangement, this changes the geometry in two ways. These two changes are here discussed separately, but they are in actuality inseparable.

FIG. 2d emphasizes only the first change. This first change mimics the change in geometry from FIG. 2a to FIG. 2b, that is, the deflection 106 moves the light-incident point of the strip 100c closer to the baseline 216. This in turn moves both the "quasi-normal" 206d and the light-reception location 214d to the right when compared with their positions in FIG. 2c. The line 206d is called "quasi-normal" because, as shown just below, it is not actually normal to the target 100c. The actual normal 110 is tilted by the angle α from the quasi-normal line 206d.

FIG. 2e adds in the second change. The deflection in the strip 100c changes the normal 110 to the surface of the strip 100c slightly (see also FIG. 1c). In consequence, the directed light 210 is actually hitting the strip 100c at an angle θ+α which is slightly greater than the θ of FIG. 2c. The new normal line 110 actually angles slightly down and to the left and is not strictly perpendicular to the baseline 216. This is a very small effect for most deflection measurements and can often be ignored. However, the effect of this small-angle change due to the deflection is discussed below in relation to step 318 of FIG. 3b as part of the mathematics of interpreting results to extract characteristics of the processed strip 100c.

Figure 3A:
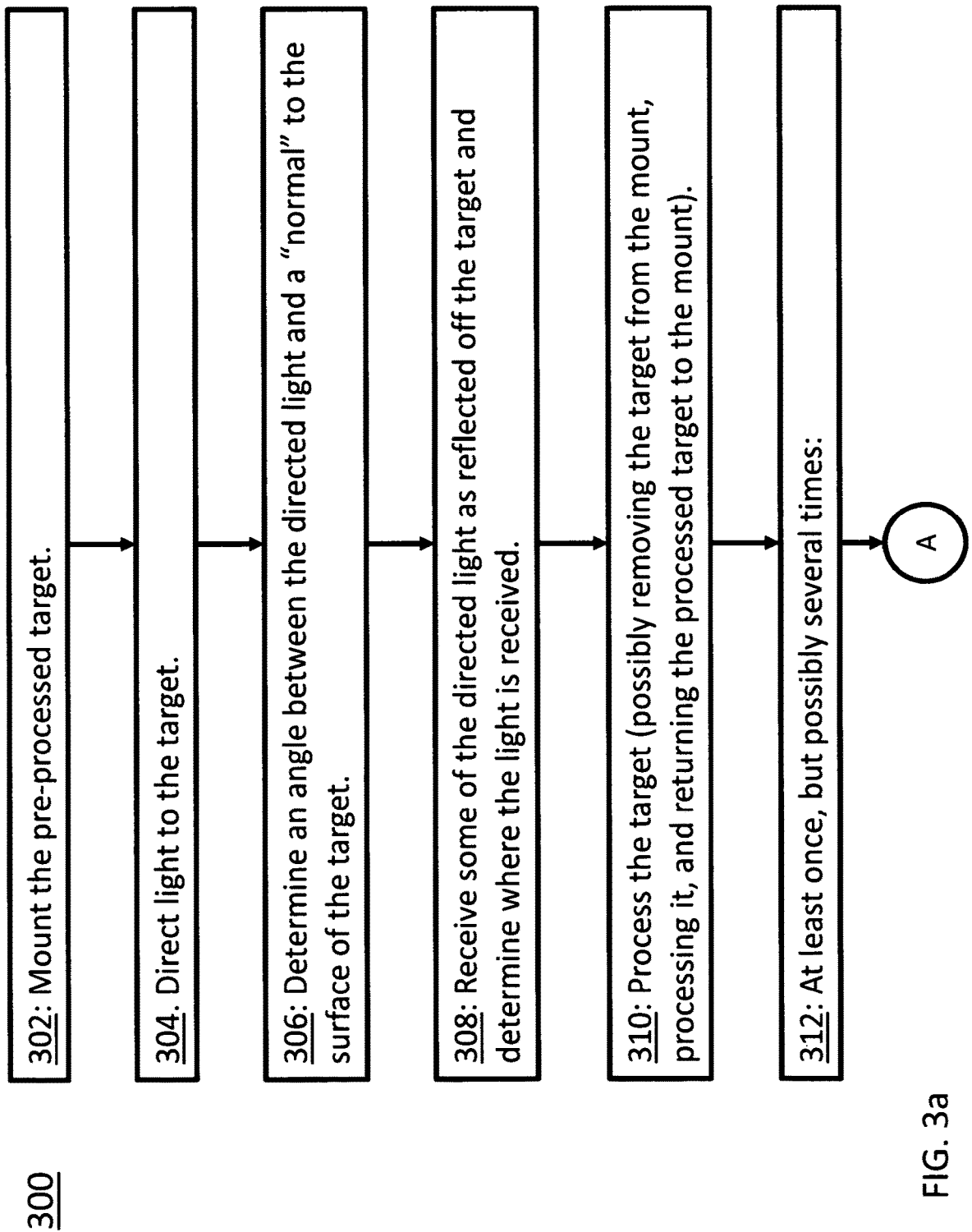
FIGS. 3a, 3b, and 3c together form a flowchart of a method for measuring the stress introduced by a process into a material strip, the method using for example, the system of FIG. 2.
Figure 3B:
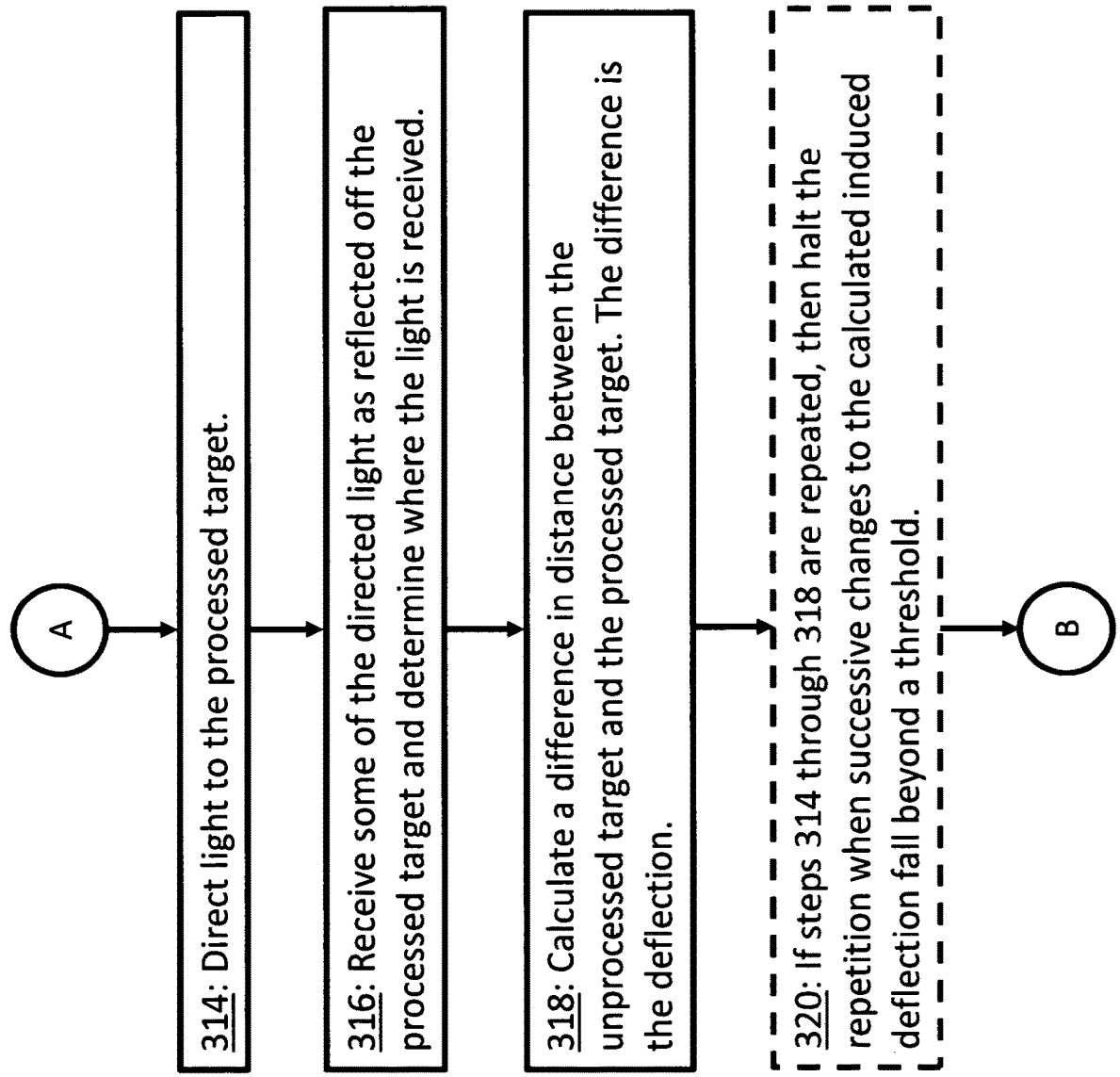
Figure 3C:
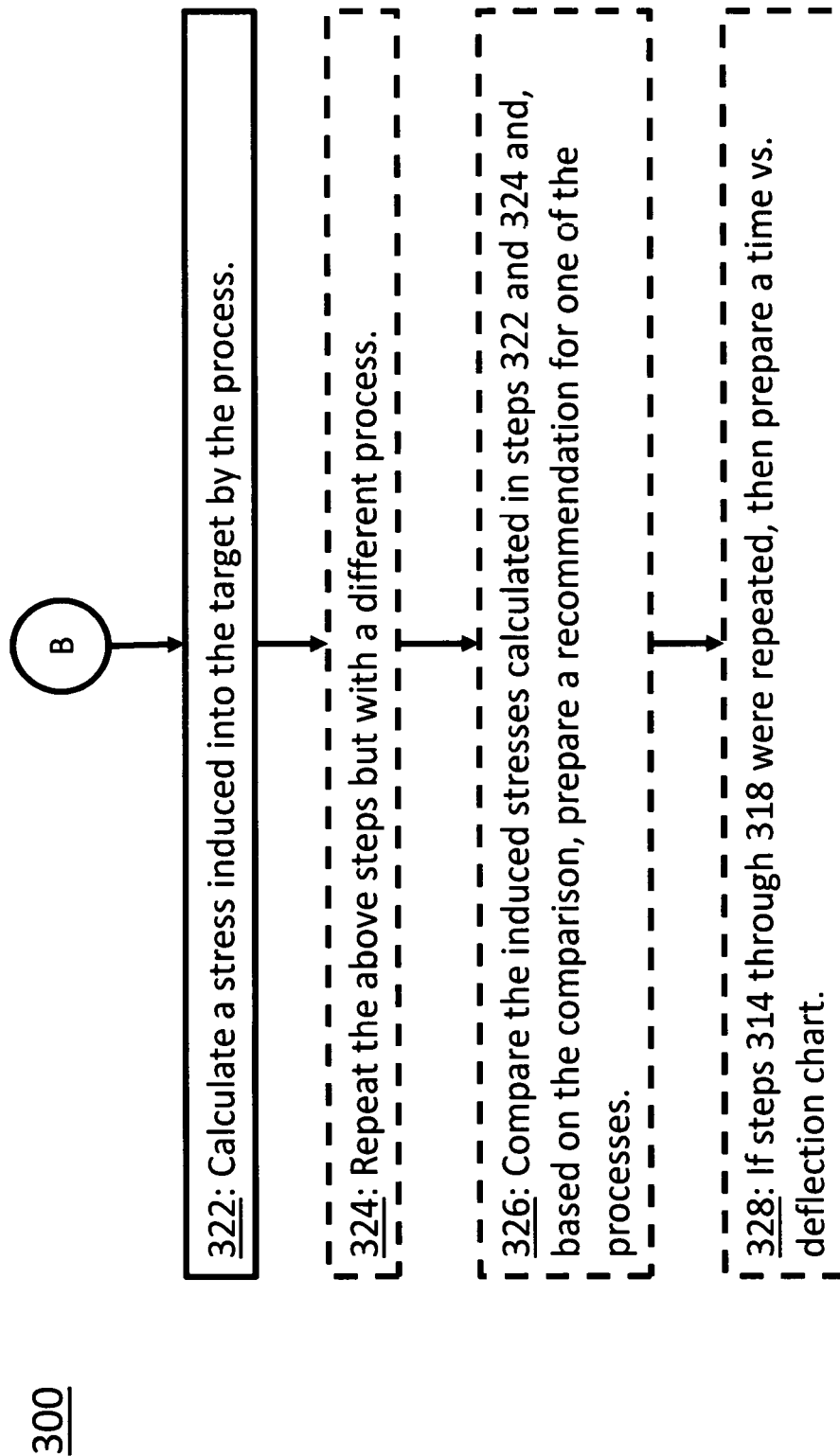

The flowchart spread over FIGS. 3a, 3b, and 3c presents one method 300 for applying the techniques of the present disclosure. While the method 300 is discussed here with respect to the representative system 200 of FIGS. 2a through 2e, the method 300 and the system 200 are not dependent upon one another. This particular method 300 calculates a stress induced into a strip 100 by processing it in a particular manner, for example by painting the strip 100 and allowing the paint to dry.

For a change of pace, the strip 100 is here called a "target." In step 302, the target 100a is attached to the mount 204. Before the processing step 310 (discussed below), the target 100a is called "pre-processed." In many situations, the pre-processed target 100a is essentially flat as shown in FIGS. 1a, 2a, and 2c.

Possibly under the control of the computer 220, the laser (or other light source) 208 directs collimated light 210 toward the pre-processed target 100a in step 304. The angle θ between the directed light 210 and the normal 206a,c to the pre-processed target 100a is set or is measured in step 306. In some situations, the angle θ is set to be as large as possible within the constraints of the system 200. Here, generally speaking, "large" means greater than 45 degrees which gives angle θ a tangent greater than 1. A "large" angle θ tends to increase the accuracy of the deflection measurement as discussed below.

Some of the directed light 210 is reflected off the pre-processed target 100a in step 308 and hits the position-sensitive light detector 212 which records the position of light reception 214a,c.

The target 100 is "processed" in step 310. There are many possibilities here. In some cases, the pre-processed target 100a is a standardized, unpainted aluminum "coupon." After the measurements of steps 302 through 308, the pre-processed coupon 100a is removed from the mount 204. It is then painted, thereby becoming a "processed" coupon 100b,c. The processed coupon 100b,c is returned to the mount 204. At this point, the importance of the mount 204 being a kinematic or gimbal mount is seen: These types of mounts 204 allow the processed coupon 100b,c to be returned to precisely the same location in the system 200 from where the pre-processed coupon 100a was removed earlier in step 310. Thus, "before" (214a,c of step 308) and "after" (214b,e of step 316) measurements can be compared to accurately characterize the change in the coupon 100.

Other exemplary processes that could involve removing the pre-processed target 100a from the mount 204 include weathering (possibly for a very long period of time), wetting, bombarding the target 100a with electromagnetic radiation (e.g., sunlight), bombarding with particles (e.g., particles meant to model cosmic-ray exposure for a panel in space), or any general modification made to the surface of the target 100.

If the system 200 is so equipped, then the processing of step 310 can be done without removing the target 100a and later re-attaching it. As just one example, if the system 200 can control its internal temperature, then the pre-processed target 100a of steps 302 through 308 could be a target 100a at a first temperature, and the processing of step 310 involves changing to a second temperature. The processed target 100b,c is then simply the target 100b,c at the second temperature.

Steps 314 and 316 (FIG. 3b) direct the light 210 toward the processed target 100b,c and record its reflected position 214b,e. As step 312 indicates, this post-processing measurement may be performed from one to any number of times. An example of multiple post-processing measurements is described below in reference to FIG. 5.

In step 318, the deflection 106 is determined for the current iteration of steps 314 and 316. The deflection 106 is the difference between (a) the distance from the baseline 216 to the pre-processed target 100a,c and (b) the distance from the baseline 216 to the processed target 100b,e.

For the pre-processed distance (a), the mathematics are the same for the top-clamp implementation of FIG. 2a and the side-clamp implementation of FIG. 2c. Let the distance from the light-reception position 214a,c along the baseline 216 to the baseline-crossing position 218 be denoted by "X(pre)," and let the distance along the normal 206a,c from the baseline 216 to the pre-processed target 100a be denoted by "Y(pre)," then it is clear that:

$$\tan(\theta) = X(\text{pre})/(2*Y(\text{pre}))$$

$$Y(\text{pre}) = X(\text{pre})/(2*\tan(\theta)) \qquad \text{Equation 2}$$

The mathematics for the processed distance (b) differ between the top-clamp implementation of FIG. 2b and the side-clamp implementation of FIG. 2e. For the top-clamp implementation, let the distance from the light-reception position 214b to the baseline-crossing position 218 be denoted by "X(post-top)," and the distance from the baseline 216 to the processed target 100b be denoted by "Y(post-top)," then it is clear that:

$$\tan(\theta) = X(\text{post-top})/(2*Y(\text{post-top}))$$

$$Y(\text{post-top}) = X(\text{post-top})/(2*\tan(\theta)) \qquad \text{Equation 3}$$

As the deflection 106 is simply the difference in distances, combining Equations 2 and 3 yields the deflection 106 caused by the processing of step 310:

$$\text{deflection } 106 = Y(\text{pre}) - Y(\text{post-top}) = (X\text{pre}) - X(\text{post-top}))/(2*\tan(\theta)) \qquad \text{Equation 4}$$

Note that the deflection 106 can be calculated directly without the intermediate step of calculating either distance. Note also that the larger the angle θ, the larger are both the numerator and denominator in Equation 4 the division of two larger numbers possibly giving more accuracy than the division of two smaller numbers.

For the side-clamp implementation of FIG. 2e, if the tilt angle α is ignored (which is often reasonable), then the processed distance calculation is the same as for the top-clamp implementation, and the deflection 106 is given by Equation 4.

Accounting for the tilt angle α makes the mathematics for the side-clamp implementation of FIG. 2e just a little trickier. Let the distance from the processed quasi-normal 206d along the baseline 216 to the baseline-crossing position 218 be "x(1)," the distance from the quasi-normal 206d along the baseline 216 to the light-reception position 214e be "x(2)," and the sum of these two be "X(post-side)." That is, $x(1)+x(2)=X$(post-side)

Denote the distance from the baseline 216 to the processed target 100c by "Y(post-side)." Then it can be shown that:

$\tan(\theta)=x(1)/Y$(post-side)

$\tan(\theta+2*\alpha)=x(2)/Y$(post-side)

$Y$(post-side)$=X$(post-side)$/(\tan(\theta+2*\alpha)+\tan(\theta))$   Equation 5

Combining Equation 5 with the pre-processed distance of Equation 2 gives:

deflection $106=Y$(pre)$-Y$(post-side)$=X$(pre)$/(2*\tan(\theta))-X$(post-side)$/(\tan(\theta+2*\alpha)+\tan(\theta))$   Equation 6

Then apply the small-angle approximation to eliminate α using Equation 1 and a measured distance 108 from the clamping point 102 to the point on the processed strip 100c where the light reflects off. This gives a solvable formula with only one unknown, the deflection 106 (Note that Equation 6 reduces to Equation 4 as a approaches 0.)

As mentioned above, a calculation of the deflection 106 based purely on the shift in the quasi-normal 206d sometimes produces a result accurate enough for the following processing (in step 322). In particular, a limitation in the precision of the output 214e of the position-sensitive light detector 212 may render the refinement based on the tilt angle α meaningless. If, however, the output 214 of the position-sensitive light detector 212 is quite precise, then the more accurate result of Equation 6 may be useful.

Figure 5:
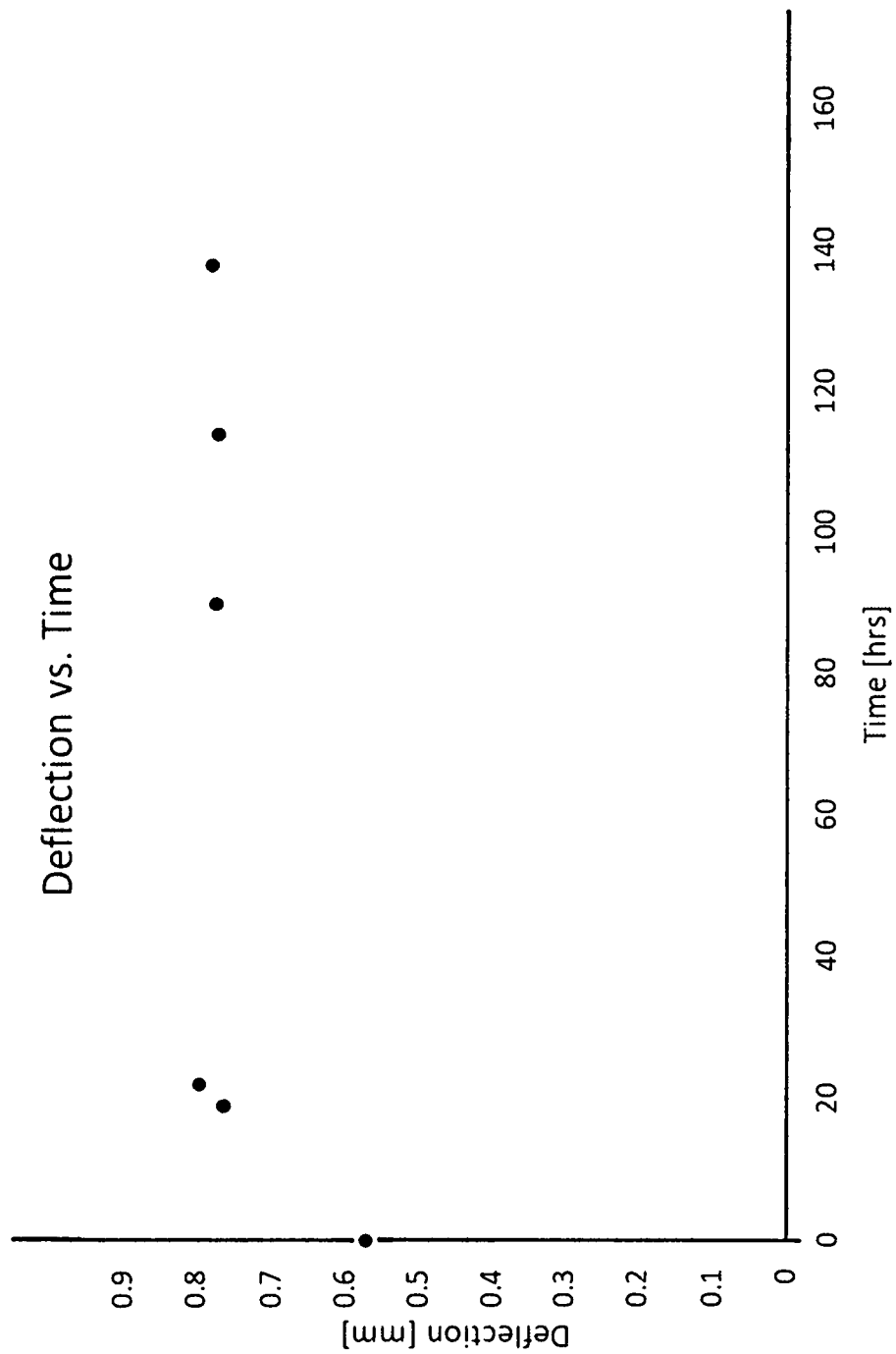
FIG. 5 is a chart showing how a deflection induced into a coupon by a representative coating process varies as the coating matures.

If steps 314 through 318 are repeated, then optional step 320 gives one way to know when to stop the repetition. Stop when the difference in the calculated deflection 106 from one repetition to the next goes beyond a set threshold. FIG. 5, discussed below, shows an application of this.

Once the one or more measurements of steps 312 through 320 are complete, the final deflection 106 is used in step 322 to calculate the stress that was introduced into the processed target 100b,c by the process of step 310. Techniques for calculating the stress based on the deflection 106 are known in the art. For example, ASTM Standard D6991; "Standard Test Method for Measurements of Internal Stresses in Organic Coatings by Cantilever (Beam) Method" is widely applicable and is incorporated herein in its entirety by reference.

Optional step 324 repeats the entire above procedure but with a different method (or methods) of processing in step 310. For example, two identical pre-processed targets 100a are painted with different paints in step 310. The resulting stresses introduced into the processed targets 100b,c are compared in step 326. If, as is often the case, minimal induced stress is a desired characteristic, then a recommendation can be made for that paint that introduces the lesser amount of stress as it dries.

Finally, in optional step 328 the computer 220 produces a time vs. deflection 106 chart showing how the deflection 106 varies as the results of the process mature (e.g., as an applied coating dries). FIG. 5, discussed below, is such a chart.

Figure 4A:
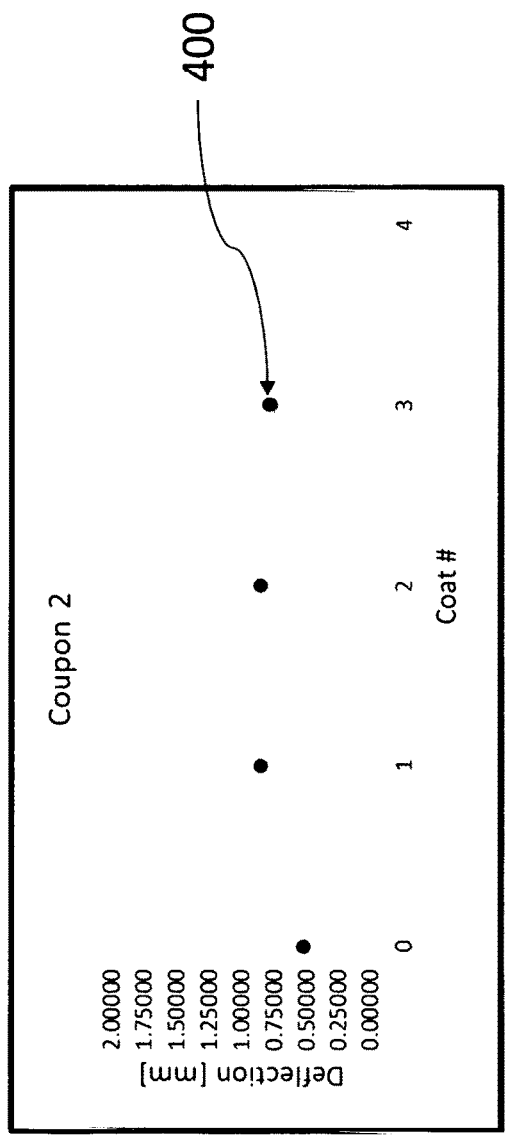
FIGS. 4a and 4b are charts showing deflections induced into coupons by repeated applications of two representative coating processes.
Figure 4B:
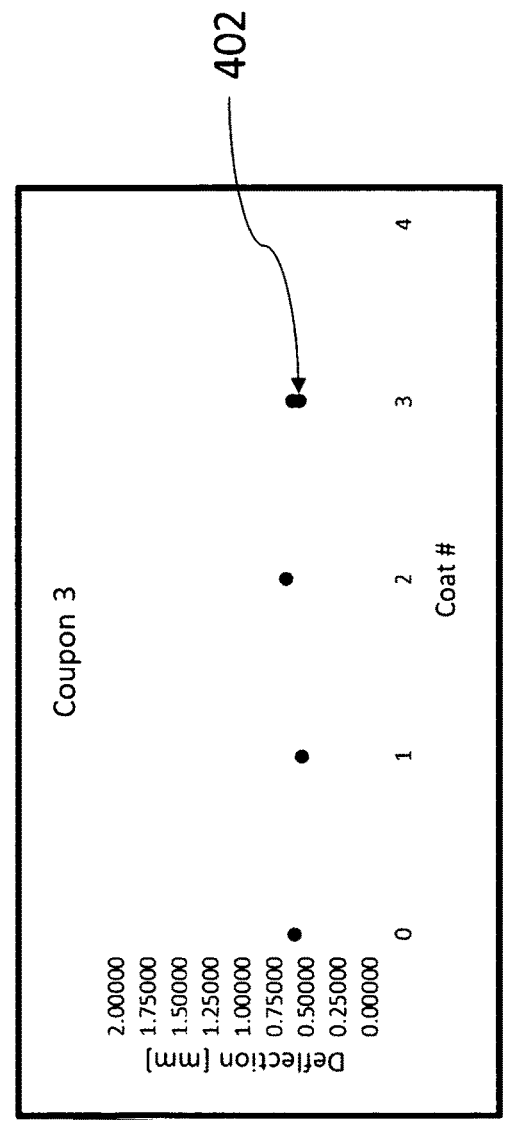

FIGS. 4a and 4b shows actual results produced by the above techniques. Two identical coupons were each processed with three coats of paint. The paint used for the two coupons was different. "Coat #0" is the pre-processed state. Note that in these examples, a non-zero deflection is listed for the pre-processed coupons. This does not mean that the pre-processed coupons are already curved, rather, this simply sets a baseline for subsequent deflection measurements Only the difference in deflection induced by the process is significant: The actual value of the "zero-point deflection" is meaningless.

The final deflections (400 and 402) were taken after the third coat had fully matured. Comparing the results, the three applications of the paint used for FIG. 4a produced a cumulative deflection 106 of about 0.30 mm, while the paint of FIG. 4b produced a cumulative deflection 106 of only about −0.05 mm. In the normal course of things, the paint of FIG. 4b would be recommended as it introduced less stress into its coupon. (Note that the negative deflection in FIG. 4b is actually quite rare: Most coatings shrink as they cure which causes a positive deflection.)

Of course, comparisons can also be made of the results produced by very different types of processes.

The time vs. deflection 106 chart of FIG. 5 is another example of results produced by the present techniques. Here, the target is processed once and then left to mature. At various intervals, the deflection 106 of the processed target 100b,c was measured. As can be seen, there was little change after about 90 hours. This example highlights the utility of the kinematic or gimbal mount 204: Because the target 100b,c could be removed, left to mature, and then accurately replaced in the system 200 for the next measurement, the processed target 100b,c can be accurately retested without tying up the entire system 200 for 140 hours.

Figure 6A:
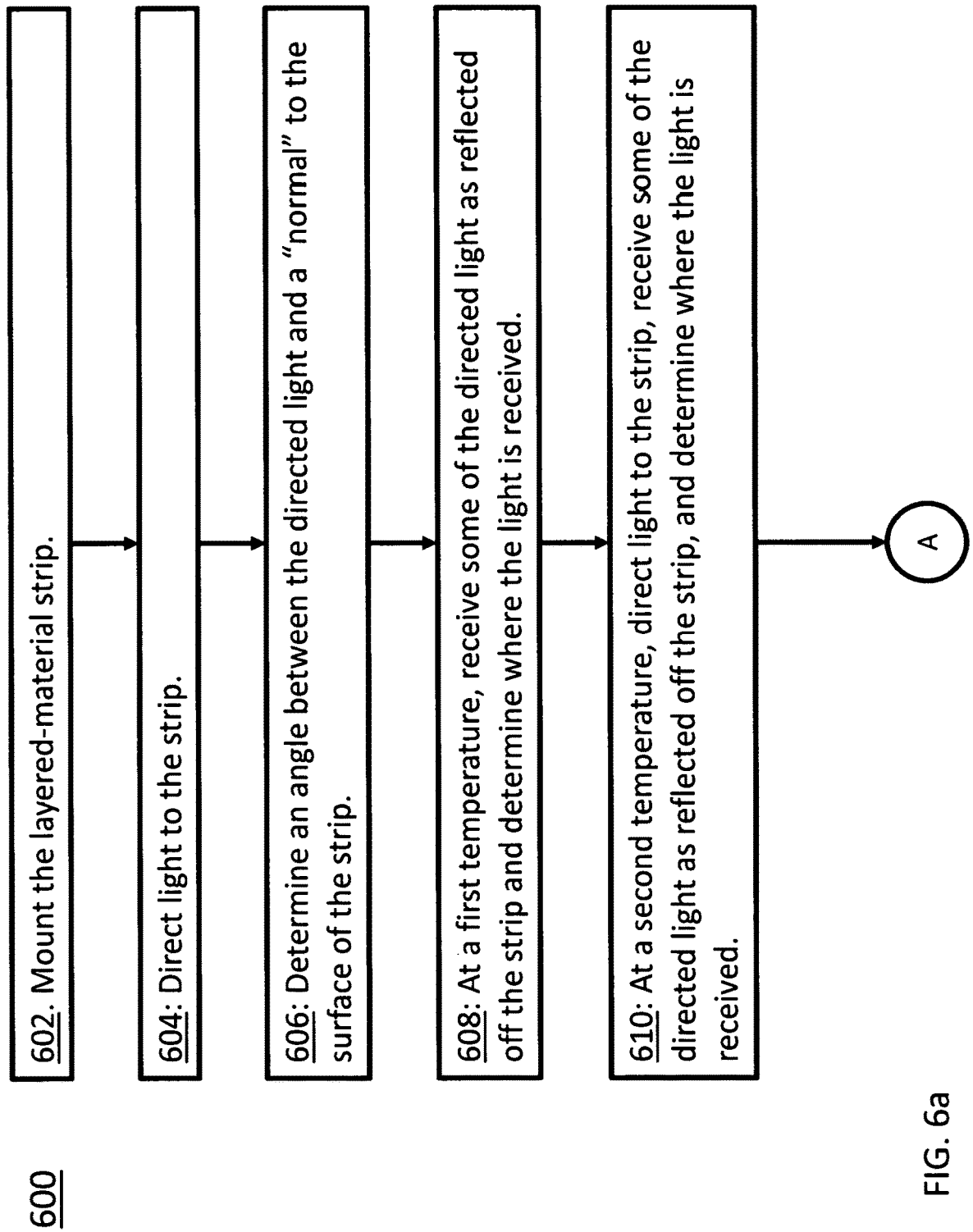
FIGS. 6a and 6b together form a flowchart of a method for measuring a characteristic of a layered-material strip based on a measured deflection and on other known characteristics of the strip.
Figure 6B:
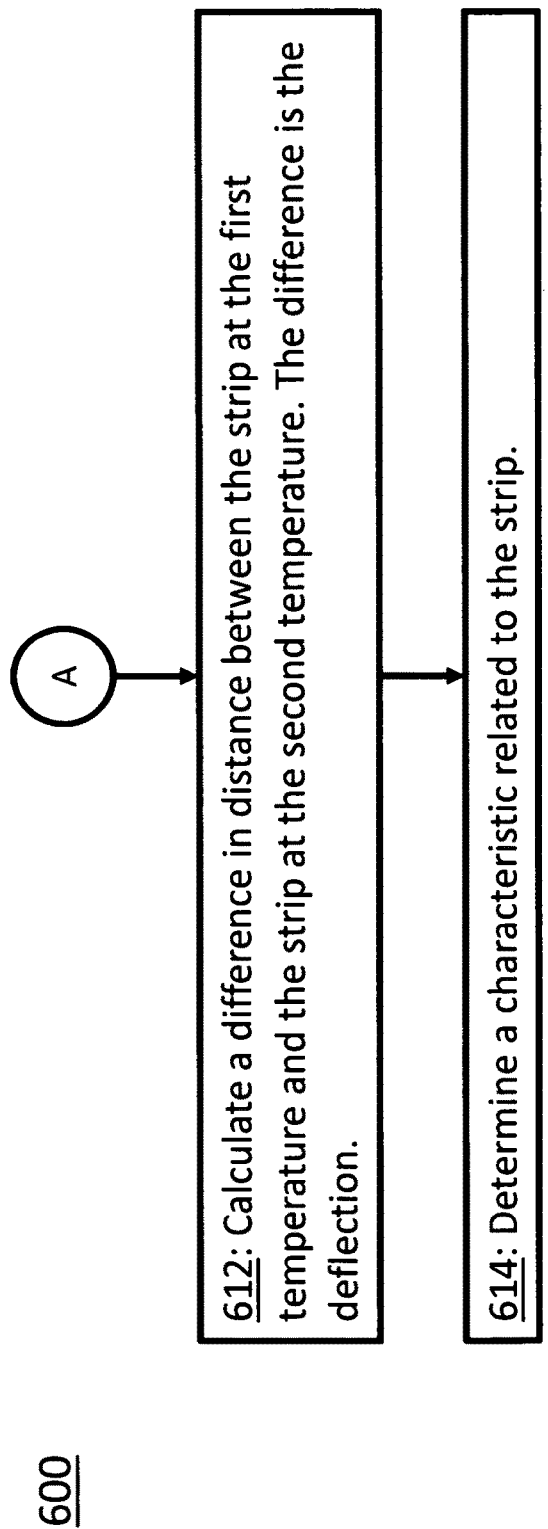

The flowchart of FIGS. 6a and 6b uses modifications of the above discussed techniques and systems for a significantly different application. Here the target 100 is a layered-material strip 100, and a method 600 is introduced to measure characteristics of the layered-material strip 100.

In some situations, the strip 100 is a bi-metallic strip 100 with one layer of say, steel, bonded to another layer of, say, brass or copper. If the two materials react differently to temperature changes, then the strip 100 bends in a manner shown by the well known Timoshenko equation. The amount of bending depends upon (i) the Young's modulus of each material in the strip 100, (ii) the thickness of each material (see 114 and 116 in FIG. 1d), (iii) the coefficient of thermal expansion of each material, and (iv) the difference in temperature from a baseline. The baseline temperature is defined as the temperature where the bi-metallic strip 100 is flat. If any six of these values (two each for (i), (ii), and (iii) because there are two materials in the bi-metallic strip 100) are known, then the seventh can be derived. For example, bi-metallic strips are used in mechanical thermometers. The six physical characteristics of their two materials are well known, so measuring the curvature of the strip accurately indicates the difference in temperature from the baseline.

The method 600 begins in step 602 where the layered-material strip 100 is affixed to the mount 204. At a first temperature, light 210 is directed to the strip 100, is reflected off, and the reflected light is received at position 214a,c at the position-sensitive light detector 212. Now the temperature is changed to a second value, and the measuring process is repeated As discussed above in reference to step 318 of FIG. 3b. the two light-reception positions 214a,c and 214b,e are used in step 612 of FIG. 6b to calculate the difference in deflection 106 caused by the change from the first to the second temperature. In step 614, the deflection 106 is used to calculate the change in curvature of the layered-material strip 100, and then the Timoshenko equation yields the unknown characteristic.

Unless explicitly stated otherwise, each numerical value and range should be interpreted as being approximate as if the word "about" or "approximately" preceded the value or range.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in the testing measurements.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

All documents mentioned herein are hereby incorporated by reference in their entireties or alternatively to provide the disclosure for which they were specifically relied upon.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

In view of the many possible embodiments to which the principles of the present discussion may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

What is claimed is:

1. A method for determining a characteristic related to a layered-material strip, the method comprising:
    mounting the layered-material strip in a position with respect to a light source and a light detector;
    at a first temperature, directing collimated first light from the light source toward the layered-material strip;
    determining an angle between the first directed light and a normal to the layered-material strip;
    first receiving some of the first directed light as reflected from the layered-material strip by the light detector;
    determining a first position where the first reflected light is received;
    at a second temperature different from said first temperature, directing collimated second light from the light source toward the layered-material strip;
    second receiving some of the second directed light as reflected from the layered-material strip by the light detector;
    determining a second position where the second reflected light is received;
    based, at least in part, on the determined angle and on the first and second determined reception positions, calculating a deflection induced into the layered-material strip wherein the change in position between where the first and second reflected light are captured is used in calculating the deflection of the material; and
    based, at least in part, on the calculated induced deflection, which is used to determine the stress introduced into the material by the temperature change, determining a characteristic related to the layered-material strip.

2. The method for determining a characteristic related to a layered-material strip of claim 1 wherein the layered-material strip comprises a first layer of steel and a second layer of a metal selected from the group consisting of: brass and copper.

3. The method for determining a characteristic related to a layered-material strip of claim 1 wherein directing collimated first light comprises directing laser light.

4. The method for determining a characteristic related to a layered-material strip of claim 1 wherein determining the angle comprises setting the angle, the setting based, at least in part, on a sensitivity threshold for the calculated induced deflection.

5. The method for determining a characteristic related to a layered-material strip of claim 1 wherein the determined characteristic is selected from the group consisting of: a Young's modulus of a material in the layered-material strip, a coefficient of thermal expansion of a material in the layered-material strip, a thickness of a material in the layered-material strip, and a difference between the first and second temperatures.

6. The method for determining a characteristic related to a layered-material strip of claim 1, further comprising:
    mounting the layered-material strip in a fixed position in translation with respect to the light source and the light detector to prevent translational movement between the layered-material strip and the light source and between the layered-material strip and the light detector.

7. The method for determining a characteristic related to a layered-material strip of claim 6, further comprising:
mounting the layered-material strip as a cantilevered strip having a fixed end clamped in place and a free end.

8. The method for determining a characteristic related to a layered-material strip of claim 6, further comprising:
mounting the layered-material strip using a kinematic mount or a gimbal mount.

9. The method for determining a characteristic related to a layered-material strip of claim 1, wherein mounting the layered-material strip comprises:
mounting the layered-material strip to a holder configured to hold the layered-material strip to the holder in a position with respect to the source of directed collimated light and the position-sensitive light detector, and configured for adjusting the angle between the first directed light and the normal to the layered-material strip and for determining the angle.

10. The method for determining a characteristic related to a layered-material strip of claim 9, wherein determining the angle between the first directed light and the normal to the layered-material strip comprises:
setting the angle based, at least in part, on a sensitivity threshold for the calculated induced deflection, the angle being set by rotating the holder holding the layered-material strip.

11. A system for determining a characteristic related to a layered-material strip, the system comprising:
a source of directed collimated light;
a holder configured for adjusting an angle between the directed light and a normal to the layered-material strip and for determining the angle;
a mount configured for holding the layered-material strip to the holder;
a position-sensitive light detector configured for receiving the directed light as reflected from the layered-material strip at a first temperature and at a second temperature different from said first temperature, and for determining a first position and a second position different from said first position corresponding, respectively, to said first and second temperatures, where the light is received, the mount configured to hold the layered-material strip to the holder in a position with respect to the source of directed collimated light and the position-sensitive light detector; and
a computing device configured for:
based, at least in part, on the determined angle and on first and second determined reception positions taken respectively at a first and at a second temperature, calculating a deflection induced into the layered-material strip wherein the change in position between where the first and second reflected light are received is used in calculating the deflection of the material; and
based, at least in part, on the calculated induced deflection which is used to determine the stress introduced into the material by the temperature change, determining a characteristic related to the layered-material strip.

12. The system for determining a characteristic related to a layered-material strip of claim 11 wherein the layered-material strip comprises a first layer of steel and a second layer of a metal selected from the group consisting of: brass and copper.

13. The system for determining a characteristic related to a layered-material strip of claim 11 wherein the source of collimated light is a laser.

14. The system for determining a characteristic related to a layered-material strip of claim 11 wherein the mount is selected from the group consisting of: a kinematic mount and a gimbal mount.

15. The system for determining a characteristic related to a layered-material strip of claim 11 further comprising:
a vibration-isolation device.

16. The system for determining a characteristic related to a layered-material strip of claim 11 wherein the determined characteristic is selected from the group consisting of: a Young's modulus of a material in the layered-material strip, a coefficient of thermal expansion of a material in the layered-material strip, a thickness of a material in the layered-material strip, and a difference between the first and second temperatures.

17. The system for determining a characteristic related to a layered-material strip of claim 11,
wherein the holder is configured for adjusting the angle between the directed light and the normal to the layered-material strip by rotational movement of the holder.

18. The system for determining a characteristic related to a layered-material strip of claim 11,
wherein the mount is configured to hold the layered-material strip to the holder in a fixed position in translation to prevent translational movement between the layered-material strip and the source of directed collimated light and between the layered-material strip and the position-sensitive light detector.

19. The system for determining a characteristic related to a layered-material strip of claim 18,
wherein the mount is configured to mount the layered-material strip as a cantilevered strip having a fixed end clamped in place and a free end.

20. The system for determining a characteristic related to a layered-material strip of claim 18,
wherein the holder is configured for adjusting the angle between the directed light and the normal to the layered-material strip by rotational movement of the holder.

* * * * *